US 7,597,881 B2

(12) United States Patent
Grüning et al.

(10) Patent No.: US 7,597,881 B2
(45) Date of Patent: Oct. 6, 2009

(54) USE OF ESTER QUATS IN COMPOSITIONS AS SAND-REPELLENT SUBSTANCES

(75) Inventors: Burghard Grüning, Essen (DE); Klaus Jenni, Essen (DE); Ralf Mathiak, Gladbeck (DE); Jürgen Meyer, Münster (DE); Christian Weitemeyer, Essen (DE)

(73) Assignee: Goldschmidt GmbH, Essen (DE)

( * ) Notice: Subject to any disclaimer, the term of this patent is extended or adjusted under 35 U.S.C. 154(b) by 253 days.

(21) Appl. No.: 11/732,450

(22) Filed: Apr. 3, 2007

(65) Prior Publication Data
US 2007/0231289 A1    Oct. 4, 2007

(30) Foreign Application Priority Data
Apr. 4, 2006    (DE)    ........................ 10 2006 015 753

(51) Int. Cl.
*C11D 1/62* (2006.01)
*C11D 1/64* (2006.01)
*C11D 1/65* (2006.01)
*C11D 1/645* (2006.01)
*C11D 1/00* (2006.01)

(52) U.S. Cl. .................................. 424/70.28
(58) Field of Classification Search ............... 424/70.28
See application file for complete search history.

(56) References Cited

FOREIGN PATENT DOCUMENTS

| DE | 4308794 C1 | 4/1994 |
| EP | 0518772 A1 | 12/1992 |
| EP | 0518773 A1 | 12/1992 |
| EP | 0750606 B1 | 1/1997 |
| EP | 1555015 A1 | 7/2005 |
| WO | WO 91/01295 | 2/1991 |

*Primary Examiner*—Johann R Richter
*Assistant Examiner*—Courtney Brown
(74) *Attorney, Agent, or Firm*—Scully, Scott, Murphy & Presser, P.C.

(57) ABSTRACT

The use of ester quats in compositions, the ester quats producing a sand-repellent action for the compositions, comprising cosmetic compositions, and the use of these cosmetic compositions having a sand-repellent action for topical application, for example for protection of the skin against ultraviolet radiation are provided. The present application in particular relates to the use of at least one ester quat based on alkanolamines in compositions, the ester quats producing a sand-repellent action for the compositions, and the acyl component of the ester quats being derived from
   (a) monocarboxylic acids,
   (b) dicarboxylic acids,
   (c) tricarboxylic acids,
or their mixtures.

5 Claims, No Drawings

USE OF ESTER QUATS IN COMPOSITIONS AS SAND-REPELLENT SUBSTANCES

FIELD OF THE INVENTION

The present invention relates to the use of ester quats based on alkanolamines as sand-repellent substances in compositions and to cosmetic compositions comprising ester quats as sand-repellent substances. Additionally, the present invention relates to the use of such cosmetic compositions for topical use with sand-repellent action, in particular for protection of the skin against ultraviolet (UV) radiation.

BACKGROUND OF THE INVENTION

The damaging action of the ultraviolet part of solar radiation on the skin is generally known to those skilled in the art. Depending on its particular wavelength, the rays have various actions on the organ skin. The "UV-C radiation" having a wavelength which is smaller than 290 nm, is absorbed by the ozone layer in the earth's atmosphere and therefore has no physiological importance. However, rays in the range between 290 nm and 320 nm, i.e., the "UV-B range", cause erythema, simple sunburn or even more or less severe burns. The narrower range around 308 nm is indicated as a maximum of the erythema activity of sunlight.

Approximately 90% of the ultraviolet radiation reaching the earth consists of UV-A rays. While the UV-B radiation varies greatly, depending on numerous factors, such as the time of year and day or latitude, the UV-A radiation, independently of time of year and day or geographical factors, remains relatively constant day by day. At the same time, the major part of the UV-A radiation penetrates into the living epidermis, while approximately 70% of the UV-B rays are stopped by the horny layer.

It is therefore of fundamental importance that cosmetic sunscreen preparations offer adequate protection both against UV-B radiation and against UV-A radiation.

The prior art is also familiar with products for the care of the skin, which are used after sunbathing and customarily contain special active ingredients, such as, for example, refatting agents and moisturizers, inflammation-relieving and cooling substances, locally anesthetizing substances and/or disinfecting substances, in order, for example, to prevent possible skin infections. These "aftersun" or "après-soleil" preparations are intended to cool the skin after sunbathing and to improve its moisturizing power, the mediation of the cooling effect playing a central role. However, the prior art lacks products which protect the skin from drying out and adequately care for it even during UV irradiation.

One disadvantage of the prior art is that customary sunscreen formulations and products for the care of the skin leave behind a film, which is usually tacky, on the skin. When using such products on a sandy beach, this has the result that the sand remains stuck to the body, which is sensed as unpleasant by the user and can lead to the sunscreen formulations and products for the care of the skin being used too little or not at all. Since a wind of greater or lesser strength usually prevails on the beach, this disadvantage as a rule occurs even if the body does not come directly into contact with the sand at all, for example when sunbathing in a wicker beach chair or deckchair, since the sand dust spun round in the wind also remains stuck to the parts of the skin on which the prior art cream has been applied.

SUMMARY OF THE INVENTION

The present invention provides novel substances and cosmetic compositions comprising these, in particular sunscreen formulations, after the use of which no sand remains stuck to the skin on which cream has been applied, or the sand adhesion is at least markedly reduced. Substances which have such a desired property are designated below as a sand-repellent.

It has been surprising and not foreseen by the person skilled in the art that in compositions the use of ester quats based on alkanolamines produces a sand-repellent action for the composition, the acyl component of the ester quat being derived from (a) monocarboxylic acids,
(b) dicarboxylic acids,
(c) tricarboxylic acids, or their mixtures.

DETAILED DESCRIPTION OF THE INVENTION

As stated above, the present invention provides compositions including cosmetic compositions that include at least one ester quat, which is based on an alkanolamine, as a sand-repellent substance. Additionally, the present invention relates to the use of such cosmetic compositions for topical use with sand-repellent action, in particular for protection of the skin against ultraviolet (UV) radiation.

The compositions comprising ester quat/s according to the invention and having sand-repellent action can contain ethanolamine, in particular triethanolamine, isopropanolamine, in particular triisopropanolamine, having a weight content of $\geq 0\%$ by weight to $\leq 5\%$ by weight, optionally $\geq 0.01\%$ by weight to $\leq 3\%$ by weight, $\geq 0.1\%$ by weight to $\leq 2\%$ by weight. It can be preferential for the content of free triethanolamine in the composition comprising ester quat to make up at most 1000 ppm.

For the preparation of the ester quats, alkanolamines according to the invention can be used which are selected from mono-, di- and/or trialkanolamines. The alkanol radical can in each case be identical or independently of one another a branched or unbranched, saturated or unsaturated hydroxyl radical having $C_1$-$C_6$ carbon atoms, preferably branched or unbranched $C_3$-$C_5$-hydroxyalkyl, branched or unbranched $C_3$-$C_5$-hydroxyalkenyl, and particularly preferably hydroxyethyl or hydroxyisopropyl.

The designation "ester quats based on alkanolamines", in the present invention also designated as "ester quats", is understood in general as meaning quaternized fatty acid alkanolamine esters and salts thereof.

Ester quats are known substances which can be obtained according to relevant methods of preparative organic chemistry. The preparation of ester quats is described, for example, in WO 91/01295, according to which triethanolamine is partially esterified with fatty acids in the presence of hypophosphorous acid, air is led through and the mixture is subsequently quaternized using dimethyl sulfate. A process for the preparation of solid ester quats is also known from German patent specification DE 4308794 C1, in which the quaternization of triethanolamine esters is carried out in the presence of suitable fatty alcohols. In a further known process for the preparation of ester quats, it is possible to start both from fatty acids, and the corresponding triglycerides in a mixture with dicarboxylic acids. Such a preparation process is described in European patent specification EP 0 750 606 B1. All of the above mentioned processes can be used in preparing ester quats for use in the present invention.

The designation "ester quat having sand-repellent action" is understood as meaning that the use according to the invention of the ester quats in compositions imparts a sand-repellent action to these, i.e., it leads, for example, to a reduction of the adhesion of sand to the skin.

Surprisingly, it has now been found that ester quats have a sand-repellent action in compositions, such that their use in cosmetic compositions, comprising sunscreen formulations, and products for the care of the skin, improve the feel of the skin on account of the reduced sand adhesion.

The cosmetic sunscreen formulations according to the invention can be used for the treatment, care and cleansing of the skin and as a makeup product in decorative cosmetics. Sunscreen formulations are also designated below as sunscreens. According to their structure, cosmetic compositions within the meaning of the present invention can be used, for example, as a skin protection cream, cleansing milk, day or night cream, etc. It is optionally possible and advantageous to use the compositions according to the invention as a base for pharmaceutical formulations. For application, the cosmetic compositions are applied to the skin in adequate amounts in the manner customary for cosmetics.

Cosmetic compositions having sand-repellent action within the meaning of this invention, also comprise dermatological compositions. Cosmetic compositions according to the invention, also designated below as dermatological compositions, whose main purpose is not protection from sunlight, can in spite of this contain a content of UV-protective substances. As is known, day creams or makeup products can contain UV-A and/or UV-B filter substances.

The ester quats and compositions comprising ester quats according to the invention show very good sensory and cosmetic properties, in particular a good dispersibility on the skin. A further advantage of the present invention is that in the case of the inventive compositions comprising ester quats for the production of a sand-repellent action of the composition, the addition of additional emulsifiers can optionally be dispensed with the ester quat/s.

In particular in the case of allergic individuals, it is important to keep the number of different components as low as possible in order to guarantee good skin tolerability. Since ester quats, as is known, have a biocidal action and the addition of emulsifiers, as described above, can optionally be dispensed with the ester quats, it is possible to make available lightscreen formulations and products for the relief and care of the skin having a reduced number of components.

Suitable mono-, di- and triester quats according to the invention, which can be used within the meaning of the invention, are products whose acyl components are derived from monocarboxylic acids of the formula RCO—OH, in which R is a linear or branched, saturated or unsaturated, optionally hydroxy-substituted acyl radical having 5 to 23 carbon atoms. Carboxylic acids suitable according to the invention are caproic acid, caprylic acid, capric acid, lauric acid, myristic acid, palmitic acid, isostearic acid, stearic acid, oleic acid, elaidic acid, arachic acid, behenic acid and erucic acid and their technical mixtures, which are obtained, for example, in the pressure cleavage of natural fats and oils.

In addition, ester quats can produce a sand-repellent action in compositions according to the invention in which at least one acyl component of the ester quat is derived from dicarboxylic acids of the formula HOOC(CH$_2$)$_n$COOH, in which n is a number from 1 to 10. Suitable dicarboxylic acids are, for example, malonic acid, succinic acid, maleic acid, fumaric acid, glutaric acid, sorbic acid, pimelic acid, azelaic acid, sebacic acid and/or dodecanedioic acid.

The use of at least one sand-repellent ester quat is preferred according to the invention, with mixtures being more preferred which contain formula I, formula II and/or formula III below:

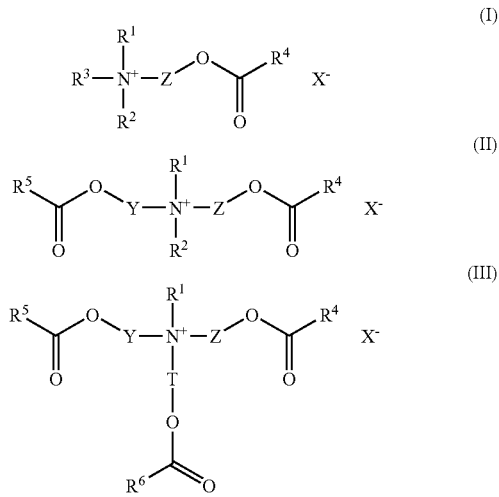

in which:
R$^1$=H, methyl, ethyl, propyl or isopropyl, preferably methyl or ethyl,
R$^2$, R$^3$=identically or independently of one another, R$^1$, a branched or unbranched saturated or unsaturated hydroxyalkyl radical having C$_1$-C$_6$ carbon atoms, preferably branched or unbranched C$_3$-C$_5$-hydroxyalkyl, branched or unbranched C$_3$-C$_5$-hydroxyalkenyl, and particularly preferably hydroxyethyl or hydroxy-isopropyl,
R$^4$, R$^5$ and R$^6$=identically or independently of one another, a branched or unbranched, saturated or unsaturated acyl radical having C$_5$-C$_{23}$ carbon atoms, preferably having C$_7$-C$_{21}$ carbon atoms, particularly preferably having C$_{11}$-C$_{19}$ carbon atoms and most preferably having C$_{15}$-C$_{17}$ carbon atoms,
T, Y and Z=identically or independently of one another, methylene, ethylene, ethenylene, branched or unbranched, saturated or unsaturated alkylene having C$_3$-C$_8$ carbon atoms, and
X=an anion, preferably the anion is a halide, alkylsulfate or alkylphosphate, and particularly preferably the anion is Cl$^-$, CH$_3$OSO$_3^-$ or CH$_3$CH$_2$OSO$_3^-$.

According to a particularly preferred embodiment of the present invention, sand-repellent ester quats can be used which are selected from di(oleylcarboxyethyl)hydroxyethylmethylammonium salt, di(tallowcarboxyethyl)hydroxyethylmethylammonium salt, N,N-di-(β-stearoylethyl)-N,N-dimethylammonium salt, N,N-di-(β-palmitoylethyl)-N,N-dimethylammonium salt, dicocoylethylhydroxyethylammonium methosulfate, di-palmoylethylhydroxyethylammonium methosulfate, dirapeseedcarboxyethylhydroxyethylammonium methosulfate, and/or disoybeancarboxyethylhydroxyethylammonium metho-sulfate and/or their hydrogenated analogs.

According to the present invention, the ester quats having sand-repellent action can be used individually or in the form of mixtures. With regard to the application properties of the sand-repellent ester quats, an average degree of esterification of 1 to 3, preferably 1.5 to 2.5, and preferably 1.7 to 2.2 has emerged as particularly advantageous for mixtures of ester quats. Furthermore, the use of sand-repellent ester quats which are technical mixtures of mono-, di- and triesters having an average degree of esterification of 1.5 to 1.9 is preferred.

For the adjustment of the desired iodine number, the ester quats can be hydrogenated according to customary processes.

It has thus been shown that sand-repellent ester quats having a high iodine number can have a markedly improved sand-repellent action compared to ester quats having a lower iodine number. The use of sand-repellent ester quats which have an iodine number of $\geq 20$ to $\leq 100$, preferably an iodine number of $\geq 30$ to $\leq 90$, and particularly preferably an iodine number of $\geq 40$ to $\leq 80$, can therefore be most preferred according to the invention. In particular, ester quats having iodine numbers in the range from $\geq 60$ to $\leq 95$ and $\geq 70$ to $\leq 85$ can have an increased sand-repellent action. The iodine number, if not stated otherwise, relates to the respective ester quat compound as such.

It has been shown that ester quats can impart a good sand-repellent action if the ester quats used have a degree of esterification of 1.5 to 2.5 and preferably of 1.7 to 2.2, and an iodine number of 20 to 60 and preferably an iodine number of 30 to 40. Particularly preferably, ester quats having a degree of esterification of 1.75 and an iodine number of 32 to 36 can be employed.

A further subject of the present invention relates to a cosmetic composition comprising ester quats having sand-repellent action, the cosmetic compositions comprising sunscreen formulations and products for the relief of skin irritation and care of the skin.

Preferably, the subject of the present invention relates to a composition having sand-repellent action, comprising ester quats for the protection of the human epidermis or a sunscreen, and its use, the cosmetic composition having sand-repellent action being present in the form of a nonionic vesicle dispersion, an emulsion, in particular an emulsion of the oil-in-water type, a cream, a milk, a gel, a gel cream, a suspension, a dispersion, a powder, a solid stick, a foam or a spray.

According to the invention, a cosmetic composition having sand-repellent action comprising ester quats and their use for making up the eyelashes, the eyebrows or the skin is also suitable, where this can be present in solid or pasty, anhydrous or aqueous form, in the form of an emulsion, of a suspension or of a dispersion.

Cosmetic compositions suitable according to the invention for topical use having sand-repellent action contain a cosmetically acceptable carrier and at least one ester quat as a sand-repellent substance.

The cosmetic compositions can contain ester quat/s as a sand-repellent substance having a weight content, based on the total weight of the cosmetic composition, of 0.1% by weight to 10% by weight, preferably of 1% by weight to 8% by weight, and particularly preferably of 2% by weight to 4% by weight.

The cosmetic compositions within the meaning of the present invention are preferably present in the form of oil-in-water (O/W) emulsions. In particular, it can be preferential for the cosmetically acceptable carrier to be present in the form of an emulsion of the oil-in-water type. The compositions within the meaning of the present invention can therefore preferably contain, beside one or more oil phases, additionally one or more water phases and, for example, be present in the form of O/W, W/O/W or manifold multiple emulsions. Such formulations can preferably also be a microemulsion, a solid emulsion, i.e., an emulsion which is stabilized by solids, e.g., a Pickering emulsion, a sprayable emulsion or a hydrodispersion.

The oil phase, for example, can be selected from the group consisting of the polar oils, comprising lecithins, fatty acid triglycerides, triglycerol esters of saturated and/or unsaturated, branched and/or unbranched alkanecarboxylic acids of a chain length of 8 to 24, in particular 12 to 18 C atoms.

The fatty acid triglycerides can be selected from the group consisting of synthetic, semisynthetic and/or natural oils, comprising cocoa glyceride, olive oil, sunflower oil, soybean oil, peanut oil, rapeseed oil, almond oil, palm oil, coconut oil, castor oil, wheatgerm oil, grapeseed oil, thistle oil, evening primrose oil and the like.

Furthermore, natural waxes of animal and vegetable origin can be used, comprising beeswax and other insect waxes, preferably berry wax, shea butter and/or lanolin.

Polar oil components can be selected from the group consisting of esters, comprising saturated and/or unsaturated, branched and/or unbranched alkane-carboxylic acids having a chain length of 3 to 30 C atoms, with saturated and/or unsaturated, branched and/or unbranched alcohols having a chain length of 3 to 30 atoms, esters of aromatic carboxylic acids, and/or with saturated and/or unsaturated, branched and/or unbranched alcohols of a chain length of 3 to 30 C atoms.

Preferred ester oils comprise octyl palmitate, octyl cocoate, octyl isostearate, octyl dodecylmyristate, octyldodecanol, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethyl-hexyl cocoate, 2-ethylhexyl isostearate, 2-ethylhexyl laurate, 2-hexyldecyl stearate, 2-octyl dodecyl-palmitate, stearyl heptanoate, oleyl oleate, oleyl erucate, erucyl oleate, erucyl erucate, tridecyl stearate, tridecyl trimellitate, and synthetic, semisynthetic and natural mixtures of such esters, in particular jojoba oil.

The oil phase, however, can also comprise dialkyl ethers and dialkyl carbonates, dicaprylyl ether and/or dicaprylyl carbonate, diethylhexyl ether and/or diethylhexyl carbonate.

Suitable oil components can be selected from the group comprising isoeicosane, neopentyl glycol diheptanoate, propylene glycol dicaprylate/dicaprate, caprylic/capric/diglyceryl succinate, butylene glycol dicaprylate/dicaprate $C_{12-13}$-alkyl lactate, di-$C_{12-13}$-alkyl tartrate, triisostearin, dipentaerythrityl hexacaprylate/hexa-caprate, propylene glycol monoisostearate, tricaprylin, dimethyl isosorbide, $C_{12-15}$-alkyl benzoate, butyloctyl salicylate, hexadecyl benzoate and butyloctyl benzoate and mixtures thereof.

As the oil phase, nonpolar oils can also be used, comprising branched and unbranched hydrocarbons and waxes, in particular mineral oil, petroleum jelly, paraffin oil, squalane and squalene, polyolefins, hydrogenated polyisobutenes and isohexadecane.

The oil phase can furthermore contain cyclic or linear silicone oils or consist completely of such oils. Systematically, the silicone oils are designated as polyorganosiloxanes. The methyl-substituted polyorgano-siloxanes, which are the quantitatively most important compounds of this group, are also designated as polydimethylsiloxane or Dimethicone (INCI). Dimethicone exists in various chain lengths and with various molecular weights.

Suitable polyorganosiloxanes according to the present invention comprise dimethylpolysiloxanes, which are obtainable, for example, under the trade names Abil® 10 to 10 000 from Goldschmidt GmbH, cetyldimethicone, hexamethylcyclotrisiloxane, polydimethylsiloxane, poly-(methylphenylsiloxane), phenylmethylpolysiloxane (INCI: Phenyl Dimethicone, Phenyl Trimethicone), cyclic silicones (octamethylcyclotetrasiloxane or decamethyl-cyclopentasiloxane), which according to INCI are also designated as Cyclomethicone, amino-modified silicones (INCI: Amodimethicones) and silicone waxes, e.g., polysiloxanepolyalkylene copolymers (INCI: Stearyl Dimethicone and Cetyl Dimethicone) and dialkoxy-dimethylpolysiloxanes (Stearoxy Dimethicone and Behenoxy Dimethicone), which are obtainable as various Abil® wax types from Goldschmidt GmbH.

The cosmetic compositions, if they are sunscreen compositions, can contain UV-A and/or UV-B filter substances. Advantageously, the compositions according to the invention contain the substances which absorb UV radiation in the UV-A and/or UV-B range, in a total amount of 0.1% by weight to 30% by weight, preferably 0.5 to 20% by weight, in particular 1.0 to 15.0% by weight, in each case based on the total weight of the compositions, in order to make available cosmetic compositions which protect the skin from the entire range of ultraviolet radiation.

The cosmetic compositions according to the invention, in particular sunscreen compositions, can contain one or more supplementary hydrophilic or lipophilic filters active in the UV-A and/or UV-B range.

Suitable organic filters are, for example, cinnamic acid derivatives, salicylic acid derivatives, camphor derivatives, triazine derivatives, benzophenone derivatives, dibenzoylmethane derivatives, diphenyl acrylate derivatives, benzimidazole derivatives, p-aminobenzoic acid derivatives, polymer filters and silicone filters.

Sunscreen filters which are active in the UV-A and/or UV-B range can be selected from: p-aminobenzoic acid, ethoxylated p-aminobenzoate, 2-ethylhexyl p-dimethylaminobenzoate, N-propoxylated ethyl p-aminobenzoate, glyceryl p-aminobenzoate, homo-menthyl salicylate, 2-ethylhexyl salicylate, tri-ethanolamine salicylate, 4-isopropylbenzyl salicylate, 4-tert-butyl-4'-methoxydibenzoylmethane, 4-isopropyldibenzoylmethane, 2-ethylhexyl 4-methoxycinnamate, methyl diisopropylcinnamate, isoamyl 4-methoxy-cinnamate, diethanolamine 4-methoxycinnamate, menthyl anthranilate, 2-ethylhexyl 2-cyano-3,3'-diphenyl-acrylate, ethyl 2-cyano-3,3'-diphenylacrylate, 2-phenylbenzimidazole-5-sulfonic acid and its salts, 3-(4'-trimethylammonium)benzylidenebornan-2-one methyl-sulfate, 1,4-benzenedi(3-methylidene-10-camphor-sulfonic acid) and its salts, urocanic acid, 2-hydroxy-4-methoxybenzophenone, 2-hydroxy-4-methoxybenzophenone 5-sulfonate, 2,4-dihydroxybenzophenone, 2,2',4,4'-tetrahydroxybenzophenone, 2,2'-dihydroxy-4,4'-dimethoxybenzophenone, 2-hydroxy-4-n-octoxybenzophenone, 2-hydroxy-4-methoxy-4'-methylbenzophenone, α-(2-oxo-born-3-ylidene)tolyl-4-sulfonic acid and salts thereof, 3-(4'-sulfo) benzylidenebornan-2-one and salts thereof, 3-(4'-methylbenzylidene)-d,l-camphor, 3-benzylidene-d,l-camphor, 2,4,6-tris[p-(2'-ethylhexyl-1'-oxy-carbonyl) anilino]-1,3,5-triazine, 2-[p-(tert-butyl-amido)anilino]-4,6-bis[(p-(2'-ethylhexyl-1'-oxy-carbonyl)anilino]-1,3,5-triazine, 1,4-bisbenzimid-azolylphenylene-3,3',5,5'-tetrasulfonic acid and salts thereof, polymer of N-[(2 and 4)-[(2-oxoborn-3-ylidene)methyl]benzyl]acrylamide, 2-[4-(diethylamino)-2-hydroxybenzoyl]alkylbenzoate, and polyorganosiloxanes having a malonate group.

The compositions having sand-repellent action which can be used according to the invention can also contain at least one agent for bronzing and/or artificial brown coloring of the skin, such as dihydroxy-acetone.

Furthermore, the cosmetic compositions according to the invention can contain pigments or alternatively nano-pigments in the range from 5 to 100 nm, preferably in the range from 10 to 50 nm, which are coated or not coated. Suitable nanopigments of metal oxides that can be employed in the instant invention comprise oxides of titanium, for example amorphous or crystalline, in the form of rutile and/or anatase, of iron, manganese, zinc, zirconium or cerium, which are all known UV lightscreen substances. Conventional coating agents can be aluminum oxide, silicon dioxide, aluminum stearate, dimethicone, and/or methicone. Nanopigments of metal oxides which can be used according to the invention and which are optionally coated are described, for example, in the patent applications EP-A-0 518 772 and EP-A-0 518 773.

Further oil-soluble UV-B and/or wide-spectrum filter substances within the meaning of the present invention comprise 3-benzylidenecamphor derivatives, preferably 3-(4-methylbenzylidene)camphor, 3-benzylidenecamphor; 4-aminobenzoic acid derivatives, preferably 4-(di-methylamino)benzoic acid 2-ethylhexyl ester, 4-di-methylaminobenzoic acid amyl ester; derivatives of benzophenone, preferably 2-hydroxy-4-methoxybenzophenone, 2-hydroxy-4-methoxy-4'-methylbenzophenone, 2,2'-dihydroxy-4-methoxybenzophenone and UV filters bound to polymers such as 3-(4-(2,2-bis-ethoxycarbonylvinyl)phenoxy)propenyl)methoxysiloxane/di-methylsiloxane copolymer.

Cosmetic compositions which can be used according to the invention can contain 0.1 to 20% by weight, preferably 0.5 to 15% by weight, and preferably 0.5 to 10% by weight, of one or more oil-soluble UV filter substances.

The cosmetic compositions can furthermore contain 0.001 to 15% by weight, preferably 0.01 to 10% by weight, particularly preferably 0.05 to 5% by weight, of additives and/or cosmetic excipients.

The cosmetic compositions according to the invention can further contain at least one additive which is selected from the fatty substances, the organic solvents, the thickening agents, the irritation-relieving agents, the antioxidants, the clouding agents, the stabilizers, the emollients, the hydroxy acids, the antifoam compositions, the hydrating agents, the vitamins, the perfumes, the preservatives, the surface-active substances, the fillers, the masking agents, the polymers, the propellants, the alkalizing agents or the acidifying agents and/or the colorants.

The cosmetic compositions according to the invention can also contain cosmetic excipients, such as are customarily used in such compositions, comprising preservatives, preservation aids, bactericides, perfumes, substances for preventing foaming, dyes, pigments which have a coloring action, thickening agents, moistening and/or moisturizing substances, fillers which improve the feel of the skin, fats, oils, waxes and/or other customary cosmetic excipients of a cosmetic formulation, comprising alcohols, polyols, polymers, foam stabilizers, electrolytes, organic solvents and/or silicone derivatives.

Cosmetic excipients which can preferably be used according to the invention comprise alcohols, ethanol and/or isopropanol, diols or polyols and their ethers, in particular propylene glycol, glycerol, ethylene glycol, ethylene glycol monoethyl or monobutyl ether, propylene glycol monom ethyl, monoethyl or monobutyl ether, diethylene glycol monomethyl or monoethyl ether and analogous products, polymers, foam stabilizers, electrolytes, dihydroxyacetone and optionally one or more thickening agents, such as silicon dioxide, aluminum silicates, polysaccharides and derivatives thereof, hyaluronic acid, xanthan gum, hydroxypropyl-methylcellulose, polyacrylates, Carbopols, for example Carbopols of the types 980, 981, 1382, 2984, 5984, in each case individually or in combination. Cosmetic excipients which can suitably be used are, for example, described in EP 1 555 015 0 A1, to which reference is fully made here.

The cosmetic composition containing sand-repellent ester quats according to the present invention can also contain moisturizers. Moisturizers are designated as substances or substance mixtures which impart the property to cosmetic compositions, after applying or dispersing on the skin surface, of reducing the release of moisture of the horny layer and/or positively influencing the hydration of the horny layer.

Moisturizers which can be used comprise glycerol, lactic acid and/or lactates, in particular sodium lactate, butylene glycol, propylene glycol, biosaccharides, glycine, soybeans, ethylhexyloxy-glycerol, pyrrolidonecarboxylic acid and urea, and polymeric moisturizers from the group consisting of the polysaccharides which are water-soluble and/or swellable in water and/or gellable with the aid of water. Hyaluronic acid, chitosan and/or a fucose-rich polysaccharide which is filed in Chemical Abstracts under the registry number 178463-23-5 and is obtainable, for example, under the name Fucogel®1000 from SOLABIA S.A. are also suitable.

Preservatives which can be used within the meaning of the present invention comprise formaldehyde-cleaving agents, iodopropyl butylcarbamates, parabens, p-hydroxybenzoic acid alkyl esters, such as methyl-, ethyl-, propyl- and/or butylparaben, phenoxyethanol, ethanol, benzoic acid. Customarily, the preservation system according to the invention furthermore advantageously also comprises preservation aids, such as, for example, octoxyglycerol, glycine, and/or soya.

Antioxidants which can be used within the meaning of the present invention comprise water-soluble antioxidants, vitamins, in particular ascorbic acid and its derivatives. Preferred antioxidants are furthermore vitamin E and its derivatives and vitamin A and its derivatives.

The amount of antioxidants, based on the total weight of the cosmetic composition, can make up 0.001 to 30% by weight, preferably 0.05 to 15% by weight, in particular 0.5 to 10% by weight.

Natural active compounds and/or their derivatives which can be used comprise alpha-lipoic acid, phytoene, D-biotin, coenzyme Q10, alpha-glucosylrutin, carnitine, carnosine, natural and/or synthetic isoflavonoids, creatine, taurine and/or β-alanine.

The cosmetic composition containing sand-repellent ester quats can also contain fillers which further improve the sensory and cosmetic properties of the formulations and, for example, produce or enhance a velvety or silky feel on the skin. Fillers which can be used comprise starch and starch derivatives, such as tapioca starch, distarch phosphate, aluminum or sodium starch, octenyl succinate, pigments which have neither mainly UV filter nor coloring action, for example boron nitride and/or Aerosils® (CAS No. 7631-86-9).

Furthermore, it can optionally be advantageous to incorporate film-forming agents into the cosmetic compositions according to the invention, for example in order to improve the water resistance of the compositions or to increase the UV-protective power. Those suitable are both water-soluble, dispersible and/or fat-soluble film-forming agents, in each case individually or in combination with one another.

Film-forming agents which can be used according to the invention comprise polyurethanes, dimethicone, copolyol, polyacrylates, PVP/NA copolymer (PVP—polyvinylpyrrolidone, VA—vinyl acetate).

Fat-soluble film-forming agents can be selected from polymers that are based on polyvinylpyrrolidone (PVP), copolymers of polyvinyl-pyrrolidone, PVP/hexadecene copolymer and/or the PVP/eicosene copolymer.

The invention is illustrated with the aid of Examples 1 to 8 below, without restricting it. The numerical values in the examples, if not stated otherwise, are percentages by weight, based on the total weight of the respective compositions.

General Test Method 0.3 g of an emulsion of Examples 1 to 8 below was applied to 150 $cm^3$ on the inside of dry, perspiration-free forearms of test individuals aged from 30 to 50 years, the respective dry forearm on inspection additionally being aerated at room temperature for 10 min and, the emulsion was homogeneously rubbed in for 2 minutes up to absorption. Subsequently, 30 ml of fine aquarium sand, obtainable from Interseroh, Article No. 388-2849, were poured onto the inside of the forearms to which the emulsion was applied for a period of 15 seconds, the sand, which was cooled to room temperature, was dried beforehand at a temperature of 80° C. in a drying oven over a period of 48 hours. Loose adhering sand was removed by clapping the hands three times. Subsequently, the adhering sand remaining on the inner surface of the forearm was rinsed off completely with ethanol and collected in a beaker. The ethanol was removed and the sand remaining in the beaker was weighed.

TABLE 1

Composition of Examples 1 to 8

| | Composition | | | | | | | |
|---|---|---|---|---|---|---|---|---|
| | 1 | 2 | 3 | 4 | 5 | 6 | 7 | 8 |
| Rewoquat ® WE 15*[1] | 3.5 | | | | 3.5 | | | |
| Rewoquat ® WE 28*[2] | | 3.5 | | | | 3.5 | | |
| Rewoquat ® WE 38 DPG*[3] | | | 3.5 | | | | 3.5 | |
| Rewoquat ® WE 18-E*[4] | | | | 3.5 | | | | 3.5 |
| Abil ® Quat 3272*[5] | | | | | 1.0 | 1.0 | 1.0 | 1.0 |
| Tegin ® M*[6] | 1.5 | 1.5 | 1.5 | 1.5 | 1.5 | 1.5 | 1.5 | 1.5 |
| Tego ® Alkanol 18*[7] | 1.0 | 1.0 | 1.0 | 1.0 | 1.0 | 1.0 | 1.0 | 1.0 |
| Tegosoft ® TN*[8] | 7.0 | 7.0 | 7.0 | 7.0 | 7.0 | 7.0 | 7.0 | 7.0 |
| Tegosoft ® DEC*[9] | 3.0 | 3.0 | 3.0 | 3.0 | 3.0 | 3.0 | 3.0 | 3.0 |
| Tegosoft ® CR*[10] | 1.0 | 1.0 | 1.0 | 1.0 | 1.0 | 1.0 | 1.0 | 1.0 |
| Tegosoft ® TIS*[11] | 1.0 | 1.0 | 1.0 | 1.0 | | | | |
| BMDM*[12] | 3.0 | 3.0 | 3.0 | 3.0 | 3.0 | 3.0 | 3.0 | 3.0 |
| EHMC*[13] | 5.0 | 5.0 | 5.0 | 5.0 | 5.0 | 5.0 | 5.0 | 5.0 |
| OC*[14] | 3.0 | 3.0 | 3.0 | 3.0 | 3.0 | 3.0 | 3.0 | 3.0 |

TABLE 1-continued

Composition of Examples 1 to 8

| | Composition | | | | | | | |
|---|---|---|---|---|---|---|---|---|
| | 1 | 2 | 3 | 4 | 5 | 6 | 7 | 8 |
| Glycerol | 3.0 | 3.0 | 3.0 | 3.0 | 3.0 | 3.0 | 3.0 | 3.0 |
| Water | 68.0 | 68.0 | 68.0 | 68.0 | 68.0 | 68.0 | 68.0 | 68.0 |
| % by weight | 100 | 100 | 100 | 100 | 100 | 100 | 100 | 100 |

Rewoquat ® WE 15*[1]: di(oleylcarboxyethyl)hydroxyethyl-methylammonium methosulfate obtainable from Goldschmidt Rewo GmbH & Co. KG.
Rewoquat ® WE 28*[2]: di(palmoyl)hydroxyethylmethyl-ammonium methosulfate + isopropanol obtainable from Goldschmidt Rewo GmbH & Co. KG.
Rewoquat ® WE 38 DPG*[3]: di(palmoyl)hydroxyethylmethyl-ammonium methosulfate + di-propylene glycol obtainable from Goldschmidt Rewo GmbH & Co. KG.
Rewoquat ® WE 18-E*[4]: di(palmoyl)hydroxyethylmethyl-ammonium methosulfate + ethanol obtainable from Goldschmidt Rewo GmbH & Co. KG.
Abil ® Quat 3272*[5]: alpha-omega-quaternized polydi-methylsiloxane, obtainable from Goldschmidt GmbH.
Tegin ® M*[6]: glyceryl stearate, obtainable from Goldschmidt GmbH.
Tego ® Alkanol 18*[7]: $C_{18}$-alcohol, obtainable from Goldschmidt GmbH.
Tegosoft ® TN*[8]: $C_{12}$-$C_{15}$-alkyl benzoate, obtainable from Goldschmidt GmbH.
Tegosoft ® DEC*[9]: dihexyl ethyl carbonate, obtainable from Goldschmidt GmbH.
Tegosoft ® CR*[10]: cetyl ricinoleate, obtainable from Goldschmidt GmbH.
Tegosoft ® TIS*[11]: triisostearin, obtainable from Goldschmidt GmbH.
BMDM*[12]: butylmethoxydibenzoylmethane.
EHMC*[13]: ethylhexyl methoxycinnamate.
OC*[14]: octocrylene.

The compositions of Examples 1 to 8 were obtained by mixing the respective components, as indicated in Table 1.

The sand-repellent compositions according to the invention of Examples 1 to 8 were in each case applied to the forearm inner surface on, in each case, 10 test individuals from the 30 to 50 age group according to the general test method described above and the sand adhesion was determined as described, the respective mean value for each cosmetic composition of Examples 1 to 8 was calculated from the respective 10 sand adhesion tests.

As a comparison test, 10 further test individuals were treated according to the general test method described above with a sunscreen Ombra® obtainable from ALDI Süd (Aldi Einkauf GmbH & Co. oHG, Essen, Germany) and the sand adhesion was determined. The results, in each case averaged, were assessed for Examples 1 to 8 and the comparison example in Table 2.

TABLE 2

| Examples | Sand-repellent action |
|---|---|
| 1 | + |
| 2 | ++ |
| 3 | +++ |
| 4 | ++++ |
| 5 | + |
| 6 | +++ |
| 7 | ++ |
| 8 | ++++ |
| Sunscreen composition Ombra ® | -- |

+ = good sand-repellent properties <1 g
++ to +++ = very good sand-repellent properties <0.5 g
++++ = best sand-repellent properties <0.3 g
− = poor sand-repellent properties >1 g
−− = very poor sand-repellent properties >1.5 g The best result in each case for Examples 1 to 8 and the comparison example are shown in Table 3.

TABLE 3

| Examples | Sand-repellent action as sand residue in [g], determined after removal of the alcohol |
|---|---|
| 1 | <0.9 |
| 2 | <0.6 |
| 3 | <0.55 |
| 4 | <0.25 |
| 5 | <1.1 |
| 6 | <0.6 |
| 7 | <0.8 |
| 8 | <0.4 |
| Sunscreen composition Ombra ® | >1.6 |

Screen Analysis

The batches of the fine aquarium sand used in each case, obtainable from Interseroh, Article No. 388 2849, were subjected first to a screen analysis, which is indicated below:

26% by weight-34% by weight have a particle size of <0.315 mm,

42% by weight-50% by weight have a particle size of >0.315 mm,

19% by weight-24% by weight have a particle size of >0.5 mm, 0.5% by weight-3% by weight have a particle size of >0.8 mm.

It is obvious that the aquarium sand, in spite of a different particle size distribution of the respective batches used, had a total weight of 100% by weight per batch.

Reference is made fully to the citations and patent applications/patents mentioned in this description and they are a complete inventory, as regards contents, of this application.

While the invention has been described herein with reference to specific embodiments, features and aspects, it will be recognized that the invention is not thus limited, but rather extends in utility to other modifications, variations, applications, and embodiments, and accordingly all such other modifications, variations, applications, and embodiments are to be regarded as being within the spirit and scope of the invention.

What is claimed as new is:

1. A method for reducing the amount of sand that is stuck to skin comprising applying a composition that includes at least one ester quat that is based on an alkanolamines to the skin, said at least one ester quat producing a sand-repellent action for the composition, wherein the at least one ester quat has an acyl component that is derived from
   (a) monocarboxylic acids,
   (b) dicarboxylic acids,
   (c) tricarboxylic acids,
or their mixtures.

2. The method as claimed in claim 1, wherein the at least one ester quat has at least one of formula I, formula II and formula III below:

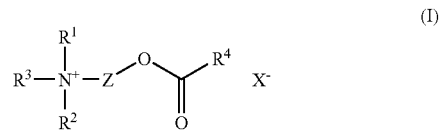

(I)

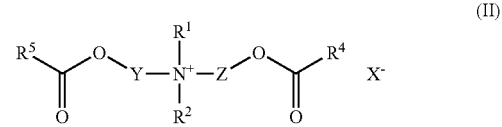

(II)

-continued

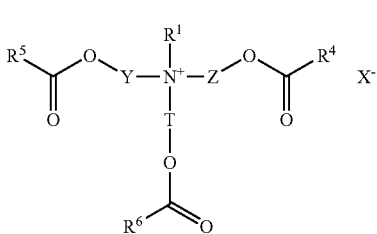

(III)

in which:

$R^1$=H, methyl, ethyl, propyl or isopropyl $R^2$, $R^3$=identically or independently of one another, $R^1$, a branched or unbranched, saturated or unsaturated hydroxyalkyl radical having $C_1$-$C_6$ carbon atoms, or a branched or unbranched $C_3$-$C_5$-hydroxyalkenyl, $R^4$, $R^5$ and $R^6$=identically or independently of one another, a branched or unbranched, saturated or unsaturated acyl radical having $C_5$-$C_{23}$ carbon atoms, T, Y and Z=identically or independently of one another, methylene, ethylene, ethenylene, branched or unbranched, saturated or unsaturated alkylene having $C_3$-$C_5$ carbon atoms, and X=an anion.

3. The method as claimed in claim 1, wherein the at least one ester quat is selected from the group consisting of di(oleylcarboxyethyl)hydroxyethyl-methylammonium salt, di(tallowcarboxyethyl)-hydroxyethylmethylammonium salt, N,N-di-(β-stearoylethyl)-N,N-dimethylammonium salt, N,N-di-(β-palmitoylethyl)-N,N-dimethylammonium salt, dicocoylethylhydroxyethylammonium methosulfate, dipalmoylethylhydroxyethylammonium methosulfate, dirapeseedcarboxyethylhydroxyethylammonium metho-sulfate, disoybeancarboxyethylhydroxyethyl-ammonium methosulfate and their hydrogenated analogs.

4. The method as claimed in claim 1, wherein the at least one ester quat has an average degree of esterification of 1 to 3.

5. The method as claimed in claim 1, wherein the at least one ester quat has an iodine number of $\geqq 20$ to $\leqq 100$.

* * * * *